(12) United States Patent
Horn

(10) Patent No.: US 6,291,498 B1
(45) Date of Patent: Sep. 18, 2001

(54) METHOD FOR OPTIMIZING PUPIL SIZE USING ALPHA ANTAGONIST

(76) Inventor: Gerald Horn, 1150 Heather Rd., Deerfield, IL (US) 60015

( * ) Notice: Subject to any disclaimer, the term of this patent is extended or adjusted under 35 U.S.C. 154(b) by 0 days.

(21) Appl. No.: 09/662,945

(22) Filed: Sep. 15, 2000

(51) Int. Cl.[7] .................................................. A61K 31/415
(52) U.S. Cl. ........................................... 514/385; 514/912
(58) Field of Search .................................... 514/603, 912, 514/385

(56) References Cited

U.S. PATENT DOCUMENTS

| 4,906,613 | 3/1990 | Watkins . |
| 5,134,124 | 7/1992 | Nisato et al. . |
| 5,288,759 | * 2/1994 | DeSartis ............................... 514/630 |
| 5,891,913 | 4/1999 | Sallmann et al. . |

* cited by examiner

*Primary Examiner*—Zohreh Fay
(74) *Attorney, Agent, or Firm*—Karl Bozicevic; Bozicevic, Field & Francis LLP

(57) ABSTRACT

A method for optimizing pupil size in individuals suffering from excessive pupillary dilation in dim light as well as through medication is disclosed. Alpha 1 antagonist is applied in an eye drop formulation to the eye, resulting in reduced pupil size in dim light, but less reduction in pupil size in bright light.

16 Claims, No Drawings

METHOD FOR OPTIMIZING PUPIL SIZE USING ALPHA ANTAGONIST

FIELD OF THE INVENTION

The present invention relates to a chemical formulation that is applicable to the eye. The present invention also relates to a method of optimizing pupil diameter preferentially in dim light and bright light by administering the chemical composition.

BACKGROUND OF THE INVENTION

While it is known that pupil size varies in its diameter in darkness between individuals from 3 mm to 9 mm, little attention has been paid to the effect of this difference on the night vision and vision in dim light (scotopic vision is dark adapted vision). Those with large pupils suffer from much more light scatter, glare, halo, and related aberrant focus of light rays that can make function under certain conditions of lighting very difficult.

Laser vision correction in particular has added new quality of vision difficulties for many of these individuals. Exposing the retina to light focusing from as much as nine times more surface area essentially magnifies every variation in curvature from the ideal. Currently, only direct acting miotic agents such as pilocarpine are used in an effort to decrease pupil size. Pilocarpine causes brow ache, ciliary muscle contraction and pseudo myopia, excessive dimness when first applied, and redness. Its effect lasts only a few hours, and it has known, though remote, risk of retinal detachment probably related to pull on the retina from stimulated ciliary muscle contraction. For these reasons it is rarely tolerated or considered a clinically useful alternative for patients with large pupils in dim light.

The only other medication used to affect pupil size is dapiprazole, an alpha-1 adrenergic receptor blocking agent. Dapiprazole is 5,6,7,8-tetrahydro-3-[2- (4-o,tolyl-1-piperazinyl)ethyl]-8-triazolo[4,3-a]pyridine hydrochloride. It is available in a 0.5% solution to partially counteract, or reverse, the dilation effect of phenylephrine, an adrenergic dilating agent, and the dilating and accommodation loss caused by tropicamide. In addition to producing redness upon instillation, dapiprazole has very little effect on pupil size in dim light in clinical application when used topically for this purpose, and therefore its sole use is as a treatment of iatrogenically induced mydriasis produced by adrenergic or parasympatholytic agents only.

The present invention is directed to a method for reducing pupil diameter in dim light in cases where dilation of the pupil is excessive, such as 6 mm or greater. In this process, the method of the invention does not induce ciliary contraction or any undesirable pseudomyopia that may result from taking certain medication. Also, by the method of the present invention, mydriasis of parasympatholytic agents is reversed similarly to dapiprazole. In fact it may be more effective on agents paralyzing accommodation such as 1% cylogyl, which can then be used for more complete cycloplegia and accurate prelaser refractive measurement.

To this date, no eye drop has been developed for the purpose of optimizing pupil size such as by reducing pupil diameter in dim light without undesirable side effects. The reason no eye drop has been successfully developed to accomplish this purpose is that no one recognized that the alpha-1 antagonists other than dapiprazole, none of which currently exists as a topical eye medication, and which are currently used for treatment of high blood pressure, treatment of pheochromocytoma, migraines, bladder spasm, prostate enlargement, and sexual dysfunction, might be adapted for this purpose.

Thus, there exists a need to provide an ophthalmic composition which achieves the combined requirements of comfort and pupil diameter optimization.

Actions of alpha adrenergic receptor antagonists include blocking alpha-1 receptor mediated contraction of arterial and venous smooth muscle. Alpha-2 adrenergic receptors are involved in suppressing sympathetic output, increasing vagal tone, facilitating platelet aggregation, inhibiting the release of norepinephrine and regulating metabolic effects. Alpha adrenergic antagonists have a wide spectrum of pharmacological specificities and are chemically heterogeneous.

Alkylating agents, imidazolines, piperazinyl quinazolines and indoles comprise the various chemical classes of alpha receptor antagonists. Many have both alpha-1 and alpha-2 receptor antagonist activity. For the present invention alpha-2 activity as represented by the indoles is of no clinical benefit. The alkylating agents offer potential for long term effectiveness for minimizing pupillary dilation, but are less effective and cause more redness than the imidazolines, such as phentolamine. The piperazinyl quinazolines, such as prazosin and dapiprazole, have modest effect on pupil diameter in dim light, but to date our research shows they are not as clinically effective as the imidazolines for this purpose. Development of longer lasting, more potent piperazinyl quinazolines may be clinically effective however. As phentolamine is not as strong an alpha-1 receptor antagonist as prazosin its stronger clinical benefit may relate to other related properties of the drug as well as its alpha-1 antagonism. These properties include blocking receptors for 5-HT, release of histamine from mast cells, and blockage of K+ channels. Phenoxybenzamine is similar in its chemical mediation.

SUMMARY OF THE INVENTION

The present invention is directed to a composition comprising alpha 1 antagonist and an excipient suitable for treating an eye. The composition may be in an eye drop formulation. Preferably, the alpha 1 antagonist belongs to a class of compounds belonging to the phentolamine or phenoxybenzamine groups.

The present invention is also directed to a method for optimizing pupil diameter such that the pupil diameter in dim light is no more than 200% greater than that in bright light, comprising administering a therapeutically effective amount of an alpha 1 antagonist to an eye of a person in need thereof. The optimized pupil diameter in dim light may be no more than 5 mm, and the pupil diameter in bright light may be constricted no more than 1 mm. Further, the optimized pupil diameter in dim light may be between and including 3 mm and 5 mm.

The present invention is also directed to a method for optimizing pupil diameter in dim light by minimizing its dilatation in response to less light, comprising administering a therapeutically effective amount of an alpha 1 antagonist to an eye of a person in need thereof In this method, dilatation of the pupil diameter in dim light may be minimized in response to less light compared with bright light, and the method may not induce ciliary muscle contraction. In the method of the present invention, the patient may suffer from excessively large pupils in dim light, and the patient may suffer from poor quality of vision, and the patient may be undergoing medication that results in dilatation of the pupil diameter. Alternatively, the pupil diameter of the patient may be naturally excessively dilated as a result of response to dimming of light.

The method of the invention may be carried out by directly instilling on to the eye an eye drop formulation of the invention. Optionally, the alpha 1 antagonist may be administered by contacting a contact lens, and the contact lens applied to the eye. In the method of the invention, the used alpha 1 antagonist preferably may belong to a class of compounds belonging to the phentolamine or phenoxybenzamine groups.

DETAILED DESCRIPTION OF THE INVENTION

It is well known that pupillary dilation in dim light is a teleologic adaption to allow more light to enter our eyes. Along with adaptions on the retina to scotopic, or night vision, this allows increased useful acuity over a very large range of lighting in low lit situations. Less well known is the dramatic range that exists among human beings of the degree to which pupils will dilate in dim light, ranging from maximal dilation in complete darkness of as little as 3 mm in some individuals to as high as 9 mm in others. This difference is part of the genetic makeup of an individual. When living in literal total darkness there may have been a very slight advantage to having larger pupil diameters in dim light, but whatever advantage was conferred has been lost once several advances in civilization resulted in illumination; including artificial means of background lighting, neon lights to allow signs to be more easily read, fluorescent light with its weighted blue more highly scattering component, and point sources of light caused by car headlights and traffic lights. These light sources are visible at optimal quality when sufficient corneal diameter exists to allow light to enter, such as a 3 mm pupil, but less corneal diameter is used to refract light, as less light scatter is induced than 5–6 millimeters pupils or larger. The preferred optimized pupil size in dim light is according to our research about 3–5 millimeters, more preferably 4–5 millimeters.

The peripheral corneal curvature in many people is not in perfect curvature alignment with that of the central cornea. In individuals with small to moderate pupils in dim light the pupil acts as a filter so that the peripheral cornea in these cases is not a factor. But, for larger pupils in dim light, peripheral corneas may be either too steep or too flat in many cases relative to the central curvature, causing spherical aberration. These corneas are technically referred to as either prolate or oblate when imperfect. The eye drops of the present invention clinically eliminate virtually all such spherical aberration, as the peripheral corneal curvature outside of a central 4–5 mm optical zone are filtered by the treated smaller pupil in dim light and the extraneous light focused by the spherical aberration is eliminated.

Three millimeter pupils are sufficiently large to allow sufficient light to enter the eye in scotopic situations, yet provide excellent filters to minimize light scatter of ambient artificial light and or point sources of light. Nine millimeter pupils on the other hand, utilizing nine times more corneal surface area, induce considerable light scatter of point sources, neon lights, and fluorescent blue light. While the current state of the art within the ophthalmic and optometric professions does not recognize this distinction, and wherein refractive surgery standard of care does not recognize a distinction in pupil diameter in dim light as a predictive factor in outcome, use of the novel pharmacologic method of the present invention has demonstrated this to be so in clinical use. Tables 1 and 2 demonstrate the results of a study of alpha adrenergic antagonists on several patients.

Refractive optical aids such as glasses or contact lenses increase the degree of light scatter in scotopic situations by adding optical elements that are imperfect in that they have surfaces that scatter light. Refractive surgery on the cornea, whereby a change in contour is induced by surgical means that can include incision (RK), laser ablation (Lasik, PRK), or prosthesis (plastic segments inserted into the cornea) also adds imperfections that increase the degree of light scatter in scotopic conditions. The variables of pupil size in dim light and refractive optics adding to light scatter has created circumstances in which individuals have quality of vision difficulty navigating in scotopic situations as a result of glare, halo, and related distortions at night or in dimly lit environments of any kind.

The method of the invention utilizes a novel pharmacologic means of optimizing pupil size by reducing pupil size in dim light. Conventional teaching of eye specialists has been to use constricting agents of the pupil, such as acetylcholine or cholinesterase inhibitors to reduce pupil size. Using dilute concentrations of such agents it is possible to constrict the pupil and create improved viewing for affected individuals in scotopic environments. However, undesirable side effects of such medications, including excessive constriction initially causing severe dimming, brow ache, generalized pain, redness, and induced blurring secondary to ciliary accommodation, severely limits the value of these classes of pharmacologic agents. Retinal detachment is a known rare complication of its use.

The pharmacologic method of the present invention utilizes a class of compounds known as alpha 1 antagonists to inhibit pupillary dilation in scotopic conditions preferentially over constriction of the pupil, affecting the dilator muscles of the iris preferentially, and has no clinically significant effect on the ciliary muscle responsible for accommodation. This class of compounds has been used to treat hypertension, prevent bladder spasmodic contractions and improve urinary outflow, and treat prostate enlargement. While toxic levels of alpha 1 antagonists are known to cause pinpoint pupils, no formulation has previously been developed as a topical pharmaceutical agent to limit dilation of the iris.

A significant feature of the present invention is to employ more potent alpha antagonists, particularly alpha 1 antagonists, to allow improvement in quality of vision in dim light without negative clinical effects in normal lighting conditions. Additionally, another feature of the present invention is to reverse the effects of parasympatholytics more effectively than dapiprazole.

The composition of the present invention can be used to optimize pupil size to obtain enhanced vision acuity in dim light by reducing the pupil diameter in dim light, but which does not clinically substantially reduce the pupil size in bright light, when the pupil size does not require it to be treated to reduce the pupil size to the same extent as the pupil under dim light.

According to the invention, the optimized pupil diameter in dim light is no more than 200% greater than that in bright light. Preferably, the pupil diameter in dim light is no more than 150%, more preferably, 100%, even more preferably, 75%, still more preferably, 60%, still more preferably, 50%, and most preferably, 33% greater than that in bright light.

While the composition of the present invention can be used to optimize pupil size under any circumstances, the composition of the invention is administered to the eye of an individual to reduce naturally occurring pupillary dilation in dim light, especially in situations where the dilation is excessive to affect vision acuity. The composition of the invention can be used also to counteract pupil dilatation caused by medication.

As used in the present application, alpha 1 antagonist refers to any agent that binds to the alpha 1 adrenergic receptor, which includes alpha 1 adrenergic receptor antagonist. Preferably, the alpha 1 adrenergic receptor is iris smooth muscle dilator selective. More preferably, the alpha 1 antagonist is in the phentolamine family, known as imidazolines, an alkylating agent such as phenoxybenzamine, or a piperazinyl quinazoline with more potent alpha-1 adrenergic antagonist activity than dapirazole. Most preferably, the alpha 1 antagonist of the invention is phentolamine or phenoxybenzamine, but any alpha 1 antagonist can be used in the present invention.

Alpha 1 antagonists such as phentolamine or phenoxybenzamine. These compounds are currently used to treat pheochromocytoma, a condition in which alpha receptor stimulants such as epinephrine and norepinephrine are released throughout the body in extremely high concentration.

According to the invention, an ophthalmic composition containing an alpha 1 antagonist is advantageously applied topically to the eye, especially in the form of a solution, a suspension, an ointment, a gel or a solid insert. Such compositions comprise the active ingredient, for example, in a range of from approximately 0.01 milligrams per cc to approximately 50 milligrams per cc, preferably from approximately 0.05 milligrams per cc to approximately 20 milligrams per cc, or more preferably in the range of from approximately 0.1 milligrams per cc to approximately 10 milligrams per cc and most preferably in the range of from 1 milligram per cc to 5 milligrams per cc. The dose of the active ingredient may depend on various factors, such as mode of administration, requirement, age and/or individual condition.

A preferred concentration of 3.3 milligrams per cc is administered by placing a single drop on a moist soft contact lens, and inserting the lens for 15–45 minutes, 1× per day. Administered in this manner the drop has a 20–24 hour clinical effectiveness, and in fact appears to have cumulative affect, such that with regular usage an every other day administration via the contact lens may be all that is necessary for some patients. The contact lens dosing allows for preferential absorption within the cornea, maximizing drop utilization and minimizing mild redness that may otherwise occur as well as the remote risk of systemic absorption. The amount of phentolamine within 1 drop—less than 0.33 mg—is about 15× less than the clinically recommended dosing for testing within the body. Of this it is unlikely as much as 10% would ever reach the systemic circulation, resulting in 150× less than a typical clinical dosage. Using contact lens dosing this is estimated to be still 10× less, or 1500 times less than a typical clinical dosage. The drop may be administered in a 3.3 milligram per cc concentration directly to the eye as a recommended daily or BID dosing.

An effective drop for the purpose of the present invention, because it limits pupil dilation and does not significantly affect pupillary constriction should have significantly more effect and cause significantly increased percentage reduction in pupil diameter in patients with large pupils in dim light, whose dim light pupil exceeds their daylight pupil considerably, and much less effect on pupil diameter in patients who have a more idealized pupil diameter in dim light, where their dim light pupil is nearly equal to their daylight pupil. This is in fact the case with phentolamine as administered (see Table 2).

There are used for a corresponding ophthalmic composition customary pharmaceutically acceptable excipients and additives known to the person skilled in the art, for example those of the type mentioned below, especially carriers, stabilizers, solubilizers, tonicity enhancing agents, buffer substances, preservatives, thickeners, complexing agents and other excipients. Examples of such additives and excipients can be found in U.S. Pat. Nos. 5,891,913, 5,134,124 and 4,906,613. Such compositions are prepared in a manner known, for example by mixing the active ingredient with the corresponding excipients and/or additives to form corresponding ophthalmic compositions. The active ingredient is preferably administered in the form of eye drops, the active ingredient being conventionally dissolved, for example, in a carrier. The solution is, where appropriate, adjusted and/or buffered to the desired pH and, where appropriate, a stabilizer, a solubilizer or a tonicity enhancing agent is added. Where appropriate, preservatives and/or other excipients are added to an ophthalmic composition.

Carriers used in accordance to the present invention are typically suitable for topical or general administration, and are for example water, mixtures of water and water-miscible solvents, such as $C_1$- to $C_7$-alkanols, vegetable oils or mineral oils comprising from 0.5 to 5% by weight hydroxyethylcellulose, ethyl oleate, carboxymethylcellulose, polyvinylpyrrolidone and other non-toxic water-soluble polymers for ophthalmic uses, such as, for example, cellulose derivatives, such as methylcellulose, alkali metal salts of carboxymethylcellulose, hydroxymethylcellulose, hydroxyethylcellulose, methylhydroxypropylcellulose and hydroxypropylcellulose, acrylates or methacrylates, such as salts of polyacrylic acid or ethyl acrylate, polyacrylamides, natural products, such as gelatin, alginates, pectins, tragacanth, karaya gum, xanthan gum, carrageenin, agar and acacia, starch-derivatives, such as starch acetate and hydroxypropyl starch, and also other synthetic products, such as polyvinyl alcohol, polyvinylpyrrolidone, polyvinyl methyl ether, polyethylene oxide, preferably cross-linked polyacrylic acid, such as neutral Carbopol, or mixtures of those polymers. Preferred carriers are water, cellulose derivatives, such as methylcellulose, alkali metal salts of carboxymethylcellulose, hydroxymethylcellulose, hydroxyethylcellulose, methylhydroxypropylcellulose and hydroxypropylcellulose, neutral Carbopol, or mixtures thereof. The concentration of the carrier is, for example, from 1 to 100,000 times the concentration of the active ingredient.

The solubilizers used for an ophthalmic composition of the present invention are, for example, tyloxapol, fatty acid glycerol poly-lower alkylene glycol esters, fatty acid poly-lower alkylene glycol esters, polyethylene glycols, glycerol ethers vitamin E and vitamin E derivatives, such as Vitamin E Tocopherol Polyethylene Glycol 1000 Succinate (TPGS) or mixtures of those compounds. A specific example of an especially preferred solubilizer is a reaction product of castor oil and ethylene oxide. Reaction products of castor oil and ethylene oxide have proved to be particularly good solubilizers that are tolerated extremely well by the eye. Another preferred solubilizer is tyloxapol. The concentration used depends especially on the concentration of the active ingredient. The amount added is typically sufficient to solubilize the active ingredient. For example, the concentration of the solubilizer is from 0.1 to 5000 times the concentration of the active ingredient.

According to the present invention lower alkylene means linear or branched alkylene with up to and including 7

C-atoms. Examples are methylene, ethylene, 1,3-propylene, 1,2-propylene, 1,5-pentylene, 2,5-hexylene or 1,7-heptylene. Lower alkylene is preferably linear or branched alkylene with up to and including 4 C-atoms.

Examples of buffer substances are acetate, ascorbate, borate, hydrogen carbonate/carbonate, citrate, gluconate, lactate, phosphate, propionate, perborate and TRIS (tromethamine) buffers. Tromethamine and borate buffer are preferred buffers. The amount of buffer substance added is, for example, that necessary to ensure and maintain a physiologically tolerable pH range. The pH range is typically in the range of from 5 to 9, preferably from 6 to 8.2 and more preferably from 6.8 to 8.1.

Tonicity enhancing agents are, for example, ionic compounds, such as alkali metal or alkaline earth metal halides, such as, for example, $CaCl_2$, KBr, KCl, LiCl, NaI, NaBr or NaCl, or boric acid. Non-ionic tonicity enhancing agents are, for example, urea, glycerol, sorbitol, mannitol, propylene glycol, or dextrose. For example, sufficient tonicity enhancing agent is added to impart to the ready-for-use ophthalmic composition an osmolality of approximately from 50 to 1000 mOsmol, preferred from 100 to 400 mOsmol, more preferred from 200 to 400 mOsmol and even more preferred from 280 to 350 mOsmol.

Examples of preservatives are quaternary ammonium salts, such as cetrimide, benzalkonium chloride or benzoxonium chloride, alkyl-mercury salts of thiosalicylic acid, such as, for example, thiomersal, phenylmercuric nitrate, phenylmercuric acetate or phenylmercuric borate, parabens, such as, for example, methylparaben or propylparaben, alcohols, such as, for example, chlorobutanol, benzyl alcohol or phenyl ethanol, guanidine derivatives, such as, for example, chlorohexidine or polyhexamethylene biguanide, or sorbic acid. Preferred preservatives are cetrimide, benzalkonium chloride, benzoxonium chloride and parabens. Where appropriate, a sufficient amount of preservative is added to the ophthalmic composition to ensure protection against secondary contaminations during use caused by bacteria and fungi.

The ophthalmic compositions may comprise further non-toxic excipients, such as, for example, emulsifiers, wetting agents or fillers, such as, for example, the polyethylene glycols designated 200, 300, 400 and 600, or Carbowax designated 1000, 1500, 4000, 6000 and 10,000. Other excipients that may be used if desired are listed below but they are not intended to limit in any way the scope of the possible excipients. They are especially complexing agents, such as disodium-EDTA or EDTA, antioxidants, such as ascorbic acid, acetylcysteine, cysteine, sodium hydrogen sulfite, butyl-hydroxyanisole, butyl-hydroxytoluene or .alpha.-tocopherol acetate; stabilizers, such as a cyclodextrin, thiourea, thiosorbitol, sodium dioctyl sulfosuccinate or monothioglycerol vitamin E and vitamin E derivatives, such as Vitamin E Tocopherol Polyethylene Glycol 1000 Succinate (TPGS); or other excipients, such as, for example, lauric acid sorbitol ester, triethanol amine oleate or palmitic acid ester. Preferred excipients are complexing agents, such as disodium-EDTA and stabilizers, such as a cyclodextrin. The amount and type of excipient added is in accordance with the particular requirements and is generally in the range of from approximately 0.0001 to approximately 90% by weight.

In another embodiment of the present invention, the ophthalmic composition comprises a therapeutically effective amount of alpha 1 antagonist, a carrier, a solubilizer and another therapeutically effective pharmaceutical agent which may be, for example, an antibiotic, an antiallergic, an anesthetic, or another drug.

The following examples are offered by way of illustration of the present invention, not by way of limitation.

EXAMPLES

EXAMPLE 1

A 5 mg/ml vial of phentolamine was diluted in an artificial tear formulation to approximately 1.5 cc of solution. The artificial solution created an effective composition for reducing the pupillary diameter in dim light via topical instillation as an eye drop. This method induces mild conjunctival and episcleral blood vessels causing very slight redness to the eye.

EXAMPLE 2

The composition of Example 1 is applied as a single drop to a moist soft contact lens with no excess saline, and the medication is delivered topically over an optional 15 minute to 2 hour period, 30 minutes preferred, through wear of the soft contact lens after which time it is removed. This greatly reduces any systemic absorption of the medication, vasodilation of the vessels and minimizes redness as a result, while allowing efficient drop utilization with the most effective concentrations to reach the iris dilator muscles and minimize dilation in scotopic conditions. The loss of muscle tone of these muscles may result in very slight constriction of the pupil as well, but not sufficient to cause the dimness from a pinpoint pupil effect commonly seen with acetylcholine or cholinesterase inhibitors. There is no noticeable effect on accommodation.

Phenoxybenzamine has the advantage of creating a longer lasting alpha 1 chemical sympathectomy, reducing the frequency of application required to maintain effective scotopic viewing. Phentolamine as modified and applied requires a single instillation per day to render up to 20 to 24 hours of effect. Phenoxybenzamine formulations ranging from 0.1% to 5% have not been as effective as phentolamine, and induce much more vasodilation and congestion. Similarly, prazosin and tolamine at 0.1% to 5% exhibits slight pupillary reduction in dilation in dim light but appears to be less effective than phentolamine. Labetalol, a potent beta adrenergic receptor antagonist, consists of four isomers, two of which have some alpha-1 antagonist activity. Its S,S and S,R isomers, and in concentrations of 0.1% to 2%, 0.5% preferred, are modestly effective. Other alpha-1 antagonists such as tamsulosin, bunazosin, alfuzonsin, urapidil, ketanserin, and indoramin, in concentrations of 0.1% to 2%, with 0.5% preferred are expected to have some clinical effectiveness as well. Alpha-2 receptor antagonists, such as found in Yohimbe extract, have no effect on pupil dilation in dim light.

Neuroleptic agents such as chlorpromazine, and ergot alkaloids such as ergotamine have mild alpha-1 receptor antagonist activity and may exhibit mild effectiveness for the purposes of the present invention.

TABLE 1

Effect of Alpha Adrenergic Receptor Antagonists on Pupil Dilation

| Compound | Adrenergic receptors blocked | Effect on pupil diam. in darkness (mm) | Redness (direct topical instillation) | Duration (hrs) | Concentration |
|---|---|---|---|---|---|
| Phentolamine | α-1 | 7.5->4.0 | + | 20–40 | 3.3 mg/ml* |
| Phenoxybenzamine | α-1 | 7.5->5.5 | ++++ | 20–? | 5 mg/ml |
| Prazosin | α-1, 2 | 7.5->6 | +++ | 5–12 | 5 mg/ml |
| Dapiprazole | α-1, 2 | 7.5->7 | +++ | 5–12 | 5 mg/ml |
| Yohimbe | α-2 | 7.5->7.5 | + | 0 | 5 mg/ml |
| Tolamine | α-1 | 7.5->6 | + | 5–12 | 5 mg/ml |
| Labetalol | α-1, β | unknown | unknown | Not tested | s, r, and s, s isomers only alpha-1 antagonists |
| Bunazosin | α-1 | unknown | not avail US | Not tested | |
| Tamsulosin | α-1 | unknown | not avail US | Not tested | |

*applied via soft contact lens with 1–2 gtts applied and placed for 30 minutes before removed

TABLE 2

Effect of Phentolamine 0.35% on Pupil Diameter**

| Subject | Dim Light Pre mm | Bright Light Pre mm | Dim Light Post mm | Bright Light Post mm | Comments |
|---|---|---|---|---|---|
| NF | 7.0 | 3.5 | 4.0 | 3.0 | Night vision good pre and post |
| NB | 7.5 | 4.0 | 4.0 | 3.0 | Had glare, halos, poor night vision pre: post night = day = exc; glare = 0; halos 70% reduced; depth perception improved |
| LR | 7.5 | 3.0 | 4.0 | 2.5 | Had glare, halo's poor night vision pre: post night much improved, dim light about same. |
| GH | 3.5 | 3.0 | 3.0 | 2.5 | Night vision good pre and post |
| LH | 4.0 | 3.0 | 3.5 | 2.5 | Night vision good pre and post |

**Phentolamine 3.3 mg/cc applied as a single drop to a soft contact lens placed for 30 minutes. Application of drops morning or daytime.

Whereas particular embodiments of this invention have been described above for purposes of illustration, it will be evident to those persons skilled in the art that numerous variations of the details of the present invention may be made without departing from the invention as defined in the appended claims.

All of the references cited herein are incorporated by reference in their entirety.

What is claimed is:

1. A method of treating a human eye, comprising the steps of:
   administering to a surface of a human eye a therapeutically effective amount of an imidazoline; and
   allowing the imidazoline to reduce the human eye pupil diameter to a range from about 1 mm to about 5 mm in dim light.

2. The method of claim 1, wherein the imidazoline is in an artificial tear formulation.

3. The method of claim 1, wherein the eye is an unmedicated human eye.

4. The method of claim 3, wherein the artificial tear formulation comprising the imidazoline is characterized by inducing a redness response in the unmedicated human eye of about 1+ or less on 4+ maximum scale.

5. The method of claim 1, wherein the pupil diameter is reduced to a range of from about 3 mm to about 5 mm in dim light.

6. The method of claim 5, wherein the eye is the eye of a human patient diagnosed with excessively large pupils in dim light.

7. The method of claim 5, wherein the eye is the eye of a human patient suffering from poor quality of vision.

8. The method of claim 5, wherein the eye is an eye of a human patient which is naturally excessively dilated as a result of response to dim light.

9. The method of claim 3, wherein the imidazoline is administered by contacting a contact lens with the artificial tear formulation comprising the imidazoline and applying the contact lens to the surface of the eye.

10. The method as claimed in claim 1, wherein the imidazoline is phentolamine.

11. The method as claimed in claim 1, wherein the imidazoline is tolamine.

12. A method of reducing the diameter of a pupil of an unmedicated human eye, comprising the steps of:
   administering to the surface of the human eye an imidazoline; and allowing the imidazoline to reduce the human eye pupil diameter to a range of from about 1 mm to about 5 mm in dim light.

13. The method of claim 12, wherein the imidazoline is phentolamine.

14. The method of claim 12 wherein the imidazoline is in an artificial tear formulation.

15. The method of claim 12, wherein the administering is carried out every 24 hours.

16. The method as claimed in claim 12, wherein the administering is carried out every 48 hours.

\* \* \* \* \*

UNITED STATES PATENT AND TRADEMARK OFFICE
CERTIFICATE OF CORRECTION

| | |
|---|---|
| PATENT NO. | : 6,291,498 B1 |
| APPLICATION NO. | : 09/662498 |
| DATED | : September 18, 2001 |
| INVENTOR(S) | : Gerald Horn |

It is certified that error appears in the above-identified patent and that said Letters Patent is hereby corrected as shown below:

On the cover page please add Related U.S. Application Data information:

"Related U.S. Application Data"

"(60) Provisional Application Nos. 60/154,003 filed Sept. 16, 1999, and 60/154,893 filed on Sept. 20, 1999."

Signed and Sealed this

First Day of August, 2006

JON W. DUDAS
*Director of the United States Patent and Trademark Office*

UNITED STATES PATENT AND TRADEMARK OFFICE
CERTIFICATE OF CORRECTION

PATENT NO. : 6,291,498 B1 Page 1 of 1
APPLICATION NO. : 09/662945
DATED : September 18, 2001
INVENTOR(S) : Gerald Horn It is certified that error appears in the above-identified patent and that said Letters Patent is hereby corrected as shown below:

On the cover page please add Related U.S. Application Data information:

"Related U.S. Application Data"

"(60) Provisional Application Nos. 60/154,003 filed Sept. 16, 1999, and 60/154,893 filed on Sept. 20, 1999."

This certificate supersedes Certificate of Correction issued August 1, 2006.

Signed and Sealed this

Twelfth Day of September, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,291,498 B1 | Page 1 of 1 |
| APPLICATION NO. | : 09/662945 | |
| DATED | : September 18, 2001 | |
| INVENTOR(S) | : Gerald Horn | |

It is certified that error appears in the above-identified patent and that said Letters Patent is hereby corrected as shown below:

On the cover page please add Related U.S. Application Data information:

"Related U.S. Application Data"

"(60) Provisional Application Nos. 60/154,033 filed Sept. 16, 1999, and 60/154,893 filed on Sept. 20, 1999."

This certificate supersedes Certificate of Correction issued August 1, 2006 and September 12, 2006.

Signed and Sealed this

Twenty-eighth Day of November, 2006

JON W. DUDAS
*Director of the United States Patent and Trademark Office*